US006936069B1

(12) United States Patent
Oladipo

(10) Patent No.: US 6,936,069 B1
(45) Date of Patent: Aug. 30, 2005

(54) MUSCLE STRIPPING DEVICE

(76) Inventor: Olarewaju James Oladipo, 9 Mulberry La., Canton, MA (US) 02021

( * ) Notice: Subject to any disclaimer, the term of this patent is extended or adjusted under 35 U.S.C. 154(b) by 0 days.

(21) Appl. No.: 09/495,737

(22) Filed: Feb. 1, 2000

(51) Int. Cl.[7] ............................... A61F 2/08; B25E 1/00
(52) U.S. Cl. ......................................... 623/13.11; 7/107
(58) Field of Search ........................... 623/13.11, 13.12, 623/13.13, 13.14, 13.15, 13.16, 13.17, 13.18, 13.19, 13.2, 14.11, 14.13, 15.11, 15.12; 606/167; 7/107

(56) References Cited

U.S. PATENT DOCUMENTS 4,028,756 A * 6/1977 Couto ........................ 140/106
4,189,799 A * 2/1980 Litehizer .................... 30/90.6
D359,214 S * 6/1995 Carlson, Jr. et al. ........... D8/51

* cited by examiner

*Primary Examiner*—Corrine McDermott
*Assistant Examiner*—Hieu Phan
(74) *Attorney, Agent, or Firm*—Weingarten, Schurgin, Gagnebin & Lebovici LLP

(57) ABSTRACT

A tendon graft stripping device for use in removing the muscle attachments to a tendon while the tendon is being prepared for use as a graft during ligament and tendon reconstruction surgery is disclosed. The muscle stripping device is made from a metal or plastic block having multiple slots therein. The multiple slots, which are of various diameters and have a circular or rectangular shape, are inter-connected by much smaller grooves to allow the passage of a tendon to be stripped through the different diameter size slots.

5 Claims, 1 Drawing Sheet

20
18
18
22
10
18
12
14
30
16

MUSCLE STRIPPING DEVICE

CROSS REFERENCE TO RELATED APPLICATIONS

N/A

STATEMENT REGARDING FEDERALLY SPONSORED RESEARCH OR DEVELOPMENT

N/A

BACKGROUND OF THE INVENTION

This invention pertains, in general to a tendon preparation device employed after the harvest of a tendon graft to prepare the tendon for use in ligament and tendon reconstruction surgery. Ligament and tendon reconstruction sometimes requires the use of an autogenous tendon graft harvested from another part of the body of the patient, or of a cadaver allograft. The hamstring tendons (particularly, the gracilis and semitendinosis) are commonly used during reconstruction of the cruciate ligaments of the knee. The palmaris longus tendon and other smaller tendons of the hand are commonly harvested for tendon reconstruction surgery.

Most harvested tendons have a purely tendinous end where they are inserted into a bony attachment and a muscular end usually coinciding with the origin of the tendon. After a tendon graft is harvested, the muscular end of the tendon has to be stripped of its attached muscle. This procedure sometimes require sharp dissection with a surgical blade that is usually cumbersome and may result in sharp injuries to the surgeon. The tendon graft sometimes may also be accidentally cut resulting in an inadequate tendon length. This stripping step also prolongs the surgeon's operating time, as the step of removing the muscle attachment is tedious.

SUMMARY OF THE INVENTION

Ligand and tendon surgery are made easier with the use of the muscle-stripping device of the present invention. The device of the invention includes a unitary body having a main longitudinal axis and two or more interconnected stripping slots extending through the device body and oriented along the main axis. The slots in the body are ordered according to either increasing size or decreasing size and are interconnected by individual grooves between adjacent slots, wherein the diameter of any groove is smaller than the diameter of any slot.

The muscle stripping device of the invention can be held free-hand or in a support base for use during tendon graft preparation in tendon repair surgery. The device of the invention receives the muscular end of a tendon and permits the tendon to be slipped sequentially through slots of various sizes to allow easy stripping of the attached muscle.

DETAILED DESCRIPTION OF THE PREFERRED EMBODIMENT

Figure 1:
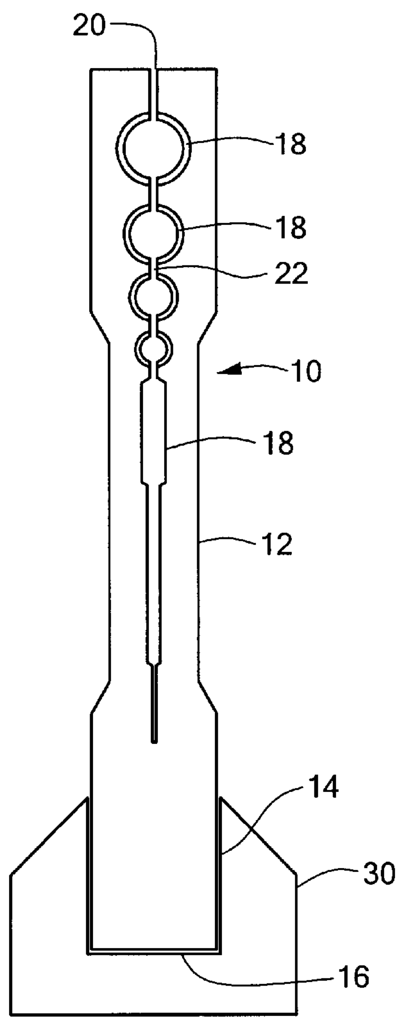
FIG. 1 is a cross-sectional schematic view of a cross-shaped muscle-stripping device of the present invention.
Figure 2:
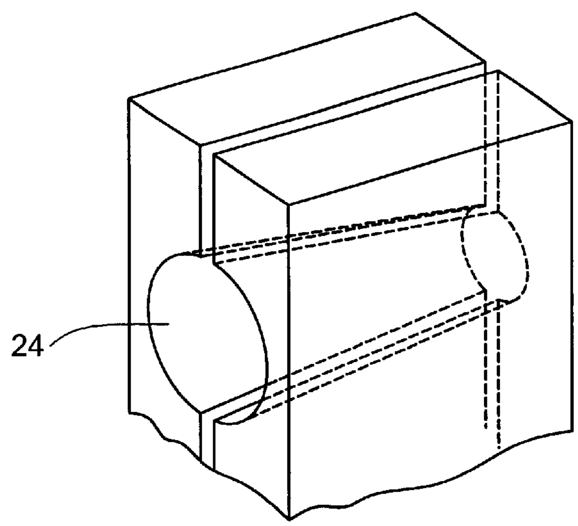
FIG. 2 is a cross-sectional schematic view of the possible orientation of the cutting edge of the stripping slot of the device.

FIGS. 1 to 2 illustrate the embodiments of the muscle-stripping device of the invention, which consists of a body 10.

As shown in FIGS. 1 and 2, body 10, consisting of an elongated block, has a handle 12, to allow free handling of the device, and a base 14, to sit into the receptacle 16 of a support base 30.

Body 10 has an access entry groove 20 of a smaller dimension to receive the narrower end of a tendon or an attached suture. This access entry groove allows the tendon to be led into the multiple slots 18 on the body 10.

Body 10 has multiple slots 18 of, e.g., circular and/or longitudinal shapes of different dimensions, allowing tendon ends as narrow as 2.5 mm or as big as 5 cm to be passed through. These slots are interconnected by longitudinal grooves 22 allowing the tendon to be drawn through slots of various sizes and diameters. Passing the tendon and its attached muscle through smaller diameter slots allows the attached muscle to be removed until only the tendon portion remains.

The slots 18 have an inner diameter varying, e.g., between 2.5 mm and 5 cm. Referring to FIG. 2, the orientation 24 of the inner wall of the slot through body 10 can be, e.g., in a cylindrical shape or a conical shape from one surface of the body to the other. The edges of the slot can be sharpened to achieve easier stripping, or can be smooth for use with delicate tendons that may be accidentally damaged.

The muscle-stripping device can be held free hand, but preferably should be used with its support base 30. The support base is in the form of a block, but could also be made of a vise grip base. The block has a cut-in receptacle to receive the base 14 in a tight fit manner without wobbling. The block also has one or more means to fasten it to the worktable to prevent it from moving as the tendon is passed through it. When a vise grip device is used, it is tightened to the base 14 to provide a secure support.

The muscle-stripping device can be made of metal, hard plastic, or any other suitable material. It can also be used in a disposable manner when made out of plastic.

To use the muscle-stripping device for detaching the attached muscle on a harvested tendon, a surgeon holds the ends of the tendons, preferably with sutures attached. The muscle-stripping device is preferably positioned in the receptacle of the support block for use. With both ends of the tendon held by the surgeon, one end of the suture is passed through the entry access groove 20 into the biggest stripping slot. In a backward and forward motion, the muscle end of the tendon is passed through to strip away any attached muscle. Care is taken to maintain the tendon in line with the slot and to avoid drawing the tendon against the edge of the slot so as not to cut the tendon. Then the attached suture is passed through the interconnecting groove into the next slot of a slightly smaller diameter. This process is continued until all the attached muscle is stripped off.

Although the invention is hereinafter described, and illustrated in the accompanying drawing figures, as being useful as a muscle-stripping device, it is to be understood that the invention's use is not limited to use with muscles and tendons, nor is it limited to the materials of which this device is manufactured, although the invention has particular advantages when manufactured of the materials described. While the foregoing has described the present invention in terms of preferred embodiments thereof, such description is not intended to limit the scope of the invention. It is expected that others skilled in the art will perceive variations which, while differing from the foregoing, do not depart from the spirit and scope of the invention as herein described and claimed.

I claim:

1. A method of stripping the muscular attachment of a harvested tendon comprising the steps of:

a. providing a muscle stripping device, said device comprising:
   i. a unitary body having a main longitudinal axis, said body furthermore having two or more interconnected stripping slots therethrough of various sizes, said slots being oriented along said main axis, wherein
   ii. said slots in said body are ordered according to either increasing size or decreasing size, and wherein
   iii. said slots are interconnected by individual grooves between adjacent slots, wherein the diameter of any said groove is smaller than the diameter of any said slot;

b. attaching a suture to each end of a harvested tendon;

c. placing the suture leader into the entry access of a stripping slot of a desired size in said device body;

c. stripping the attached muscle off of the tendon by performing a backward and forward motion through stripping slots of varying sharpness, and by passing the tendon through the interconnecting grooves into slots of different diameters and dimensions until all the attached muscles are detached.

2. A muscle stripping device for use with humans or animals to strip the muscular attachment from a harvested tendon, said device comprising:

a. a unitary body having a main longitudinal axis, said body furthermore having two or more interconnected stripping slots therethrough of various sizes, said slots being oriented along said main axis, wherein b. said slots in said body are ordered according to either increasing size or decreasing size, and wherein c. said slots are interconnected by individual grooves between adjacent slots, wherein the diameter of any said groove is smaller than the diameter of any said slot.

3. The muscle stripping device of claim 2, wherein said stripping slots are circular in shape.

4. The muscle stripping device of claim 2, wherein said stripping slots are oriented perpendicularly to said main axis.

5. The muscle stripping device of claim 2, further in combination with a support base that allows said device to be positioned in a stable manner on a support table when in use.

* * * * *

UNITED STATES PATENT AND TRADEMARK OFFICE

CERTIFICATE OF CORRECTION

PATENT NO. : 6,936,069 B1
APPLICATION NO. : 09/495737
DATED : August 30, 2005
INVENTOR(S) : Olarewaju James Oladipo It is certified that error appears in the above-identified patent and that said Letters Patent is hereby corrected as shown below:

Column 1, lines 57-61, replace the paragraphs under the section entitled BRIEF DESCRIPTION OF THE SEVERAL VIEWS OF THE DRAWINGS with the following:

--Fig. 1 is a plan view of a cross-shaped muscle-stripping device of the present invention; and Fig. 2 is a perspective view of a possible orientation of the inner wall of a stripping slot through the device of the invention according to Fig. 1.--;

Column 2, line 3, “receptacle 16” should read --receptacle area 16--;

Column 2, line 20, “orientation 24 of” should read --orientation of--;

Column 2, line 21, “of the slot” should read --of a slot 18--; and

Column 2, line 22, “shape from” should read --shape 24 from--.

Signed and Sealed this

Twenty-first Day of November, 2006

JON W. DUDAS
*Director of the United States Patent and Trademark Office*